United States Patent [19]

Wilson

[11] Patent Number: 4,737,317
[45] Date of Patent: Apr. 12, 1988

[54] PROCESS FOR PREPARING PHENYLDICHLOROPHOSPHINE

[75] Inventor: Glenn R. Wilson, Altamount, Ill.

[73] Assignee: Monsanto Company, St. Louis, Mo.

[21] Appl. No.: 566,016

[22] Filed: Dec. 27, 1983

[51] Int. Cl.$^4$ ................................................. C07F 9/52
[52] U.S. Cl. .................................................. 260/543 P
[58] Field of Search .................................. 260/543 P

[56] References Cited

U.S. PATENT DOCUMENTS

| | | | |
|---|---|---|---|
| 3,029,282 | 4/1962 | Toy et al. | 260/543 |
| 3,057,917 | 10/1962 | Maier | 260/543 |
| 3,210,418 | 10/1965 | Planfetti | 260/543 |
| 3,864,394 | 2/1975 | Via et al. | 260/543 P |
| 3,954,859 | 5/1976 | Jurewicz et al. | 260/543 P |

FOREIGN PATENT DOCUMENTS 443354  2/1969  Japan.

OTHER PUBLICATIONS

Kosolapoff, G. M. et al., *Organic Phosphorus Compounds*, (1973), vol. 4, pp. 79–82, (Wiley–Interscience, Publ.).

*CRC Handbook of Chemistry and Physics*, (1979–1980 Ed.), CRC Press, Publ., pp. B–105 and C–146.

*Organic Syntheses*, Coll., vol. 4, 784–785, (1963).

*Primary Examiner*—Donald B. Moyer
*Assistant Examiner*—L. Hendriksen
*Attorney, Agent, or Firm*—Wendell W. Brooks; Arthur E. Hoffman; Arnold H. Cole

[57] ABSTRACT

Phenyldichlorophosphine is prepared by contacting benzene with phosphorus trichloride in the vapor phase at a temperature from about 100° C. to about 145° C. in the presence of a catalyst consisting essentially of aluminum metal and an activating amount of aluminum chloride.

9 Claims, No Drawings

PROCESS FOR PREPARING PHENYLDICHLOROPHOSPHINE

BACKGROUND OF THE DISCLOSURE

1. Field of the Invention

This invention relates to a process for the preparation of phenyldichlorophosphine. More particularly, this invention relates to a process for the vapor phase preparation of phenyldichlorophosphine at temperatures from about 100° C. to about 145° C. in the presence of a catalyst consisting essentially of aluminum metal and an activating amount of aluminum chloride.

Phenyldichlorophosphine is a very useful intermediate compound in organic synthesis. It may be used to prepare various phosphorus-containing insecticides and to prepare the corresponding phosphonous acid, $C_6H_6P(OH)_2$. Extensive quantities of phenyldichlorophosphine are used each year for these purposes.

2. Description of the Prior Art

Various processes for the preparation of aryldihalophosphines are known in the art. The preparation of aryldichlorophosphine, inter alia, is described in U.S. Pat. No. 3,954,859. In this process, an aromatic hydrocarbon selected from benzene, toluene, and xylene is reacted with phosphorus trichloride in the presence of a crystalline aluminosilicate zeolite in the hydrogen form catalyst at a temperature from 147° to 475° C. In this reaction, benzene and phosphorus trichloride yield phenyldichlorophosphine.

In U.S. Pat. No. 3,864,394 is described a process wherein phenyldichlorophosphine (phenylphosphonous dichloride) is prepared by reacting chlorobenzene, phosphorus trichloride, and elemental phosphorus in an autoclave at a temperature from about 275° C. to about 400° C. for a period of time from about 0.25 hour to about 30 hours.

U.S. Pat. No. 3,210,418 discloses the preparation of phenyldichlorophosphine by reacting benzene with phosphorus trichloride at a temperature of 725° C. in the presence of a homogeneous gaseous catalyst, for example, molecular oxygen, halogens, or nitrogen oxides, which function as a free radical promoter.

In U.S. Pat. No. 3,057,917 is described a process for preparing, inter alia, arylhalophosphines which comprises reacting an aryl halide, in the vapor phase, with red phosphorus in the presence or absence of a metal catalyst selected from the group consisting of copper, nickel, silver, tin, antimony, and alloys of copper with at least one other metal of the group of metals. The aryldihalophosphine reportedly is the predominant species.

U.S. Pat. No. 3,029,282 describes a process for the preparation of phenyldichlorophosphine wherein benzene and phosphorus trichloride are reacted at temperatures of at least 350° C. in the presence of chlorobenzene. The presence of chlorobenzene reportedly increases the reaction rate, decreases decomposition products, and improves the quality of the phenyldichlorophosphine.

In Japanese Pat. No. Sho 44[1969]-3354 a process for the preparation of phenyldichlorophosphine is described wherein benzene and phosphorus trichloride are reacted at a temperature of 550° C. to 850° C. in the presence of carbon tetrachloride.

Finally, in an article in *Organic Syntheses, Coll.* Vol. 4, 784–785 (1963), there is disclosed a process for the preparation of phenyldichlorophosphine which comprises reacting in the liquid phase a homogeneous solution of benzene, phosphorus trichloride, and aluminum chloride at reflux temperatures, and treating the resulting hot reaction mixture with phosphorus oxychloride.

Although these prior art processes generally provide the desired product, they nevertheless are limited in their application. Principal among these limitations, are the drastic and severe reaction conditions which must be employed which leads to the substantial production of decomposition products. The discovery of the relatively low temperature, vapor phase process of the present invention is therefore believed to be a decided advance in the state of the art.

SUMMARY OF THE INVENTION

This invention is directed to a process for the vapor phase reaction of benzene and phosphorus trichloride at temperatures from about 100° C. to about 145° C. in the presence of a catalyst consisting essentially of aluminum metal and an activating amount of aluminum chloride. Accordingly, typical objects of this invention are to provide a relatively low-temperature vapor phase process for the preparation of phenyldichlorophosphine and to provide a vapor phase process for preparing phenyldichlorophosphine at temperatures from about 100° C. to about 145° C. characterized by high reactant conversions and high phenyldichlorophosphine selectivity.

These and other objects, aspects, and advantages of the invention, which will become apparent to those skilled in the art from the accompanying description and claims are achieved by the process disclosed herein for the preparation of phenyldichlorophosphine which comprises contacting benzene with phosphorus trichloride in the vapor phase at a temperature from about 100° C. to about 145° C. in the presence of a catalyst consisting essentially of aluminum metal and an activating amount of anhydrous aluminum chloride.

DESCRIPTION OF THE PREFERRED EMBODIMENTS

In accordance with this invention, phenyldichlorophosphine (also known as phenylphosphonous dichloride) is prepared by a vapor phase process which comprises contacting benzene with phosphorus trichloride in the vapor phase at a temperature from about 100° C. to about 145° C. in the presence of a catalyst consisting essentially of aluminum metal and an activating amount of aluminum chloride. The process is characterized by high reactant conversion and high phenyldichlorophosphine selectivity.

The catalyst essential for use in the present invention consists essentially of aluminum metal and an activating amount of aluminum chloride. The aluminum metal can exist in any convenient form which can provide the necessary surface to catalyze the desired reaction between the benzene and the phosphorus trichloride to yield phenyldichlorophosphine. Suitable forms for the aluminum metal include aluminum wire (conveniently shaped into a coil) and particulate aluminum metal. In general, aluminum wire is preferred.

The amount of aluminum metal employed in the instant process is not narrowly critical. All that is necessary is that the aluminum metal is employed in an amount sufficient to catalyze the reaction between the benzene and phosphorus trichloride. Although larger or smaller amounts can be employed, if desired, an amount of aluminum from about 0.10 mole to about 1.0 mole per mole of phosphorus trichloride is generally sufficient, with about 0.40 mole to about 0.70 mole being preferred.

In addition to the aluminum metal, the catalyst also includes a catalyst activating amount of aluminum chloride. The actual amount of aluminum chloride employed is not critical. All that is necessary is that an amount sufficient to activate the catalyst and initiate reaction between the benzene and phosphorus trichloride is present. A trace amount, for example, 0.000010 to 0.0010 gram per gram of aluminum metal, is usually sufficient although, if desired, both larger and smaller amounts may be employed.

As previously noted, contact of the benzene with the phosphorus trichloride in the presence of the catalyst is effected in the vapor phase. The benzene and phosphorus trichloride are heated to the vaporization temperature at atmosphereic pressures and the vaporous mixture is brought into contact with the catalyst which is located in a reaction zone previously heated to the desired reaction initiation temperature. Suitable reaction initiation temperatures (and actual reaction temperatures) range from about 100° C. to about 145° C.

Once the reaction is initiated, the heat of reaction from the exothermic reaction is sufficient to maintain the reaction at a temperature of about 115±5° C. without the application of additional heat to the reaction zone. However, if a higher reaction temperature, for example, in excess of about 120° C. up to about 145° C., is desired, additional heat must be supplied to the reaction zone to maintain such higher temperature. In general, and as a practical matter, initiation of the reaction at about 100° C. and maintenance of the reaction temperature at about 115±5° C. are preferred in that less energy is required to carry out the reaction.

The process of this invention is conducted under substantially anhydrous conditions under an inert atmosphere, for example, nitrogen, helium, argon, and the like, with nitrogen generally being preferred for practical reasons. The carrying out of the reaction under substantially anhydrous conditions is necessary in order to avoid the ready hydrolysis of the phosphorus trichloride reactant. As employed herein, the term "substantially anhydrous" means not more than one weight percent water is present in the reaction.

The reaction of benzene with phosphorus trichloride to form phenyldichlorophosphine involves reaction of one mole of benzene with one mole of phosphorus trichloride. Accordingly, the reaction may be carried out employing one mole of benzene for each mole of phosphorus trichloride. However, it is preferred to employ a molar excess of benzene over the phosphorus trichloride. A suitable mole ratio of benzene to phosphorus trichloride for carrying out the reaction, therefore, ranges from about 1.0 to to about 10.0 or higher, with mole ratios from about 3.0 to about 5.0 being preferred.

The present process may be conducted as a batch operation or a continuous operation. In carrying out the reaction as a batch operation, the vaporized reactants are contacted in the presence of the catalyst in a suitable reaction vessel for a term sufficient to effect a desired extent of reaction. This required time is not critical and can range from about two hours to about 10 hours, with about five hours to about eight hours being sufficient. The reaction, however, may be carried out as a continuous operation. In continuous operations, the vaporized reactant can be passed through a bed of the catalyst (aluminum metal plus an activating amount of aluminum chloride) contained in a suitable vessel. Similarly, in a continuous operation, the vaporized reactant may be contacted in the presence of a moving or ebullient bed of (particulate) catalyst.

Following the reaction of the benzene with the phosphorus trichloride, the reaction mixture is treated for the recovery of, or the gas chromatographic analysis for, the phenyldichlorophosphine product. The reaction mixture is cooled and diluted with benzene. To the resultant mixture is added a calculated amount of p-dioxane (calculated from the weight loss of the aluminum metal catalyst) to decompose the aluminum-containing phenyldichlorophosphine complex. The freed phenyldichlorophosphine product is then analyzed by gas chromatography or purified, if desired, by conventional means, for example, vacuum distillation.

It will be noted that, in addition to the aluminum-containing phenylidichlorophosphine complex, an unidentified aluminum-containing complex, assumed to be an aluminum-containing complex of diphenylchlorophosphine (from benzene and phenyldichlorophosphine), is also present in the reaction mixture. Apparently, the organic ligand is bound more tightly to the aluminum in the latter complex in that p-dioxane fails to induce the desired decomposition to permit easy and reliable analysis of such species by gas chromatography or purification by conventional means.

The following specific examples illustrating the best known methods of practicing this invention are described in detail in order to facilitate a clear understanding of the invention. It should be understood, however, that the detailed expositions of the application of the invention while indicating preferred embodiments, are given by way of illustration only and are not to be construed as limiting the invention since various changes and modifications within the spirit of the invention will become apparent to those skilled in the art from this detailed description.

EXAMPLE 1

A quartz tube arranged vertically and having a closed-loop sidearm fitted with a ground glass stoppered opening in the upper portion for insertion and removal of catalyst, a Nichrome wire heating coil for supplying heat, and a thermometer-containing thermowell for temperature measurements in the reaction zone, and a dip tube extending from a point above the lower sidearm loop to a point below the liquid level in the benzene-phosphorus trichloride vaporization flask (described below) was employed as the reactor. The tube was fitted at the lower end with a suitably-sized round bottom flask equipped with a thermometer-containing thermowell for temperature measurements for vaporizing the benzene and phosphorus trichloride reactants and at the upper end with a water-cooled reflux condenser. The reflux condenser was equipped with a three-way stopcock valve as an inlet for nitrogen and as an outlet for hydrogen chloride (HCl) evolved during the course of the reaction. The outlet was fitted in series with a dry ice-acetone cold trap and an HCl gas scrubber.

Aluminum wire [0.16 cm (0.0625 in) diameter, 8.64 g, 0.320 g-atom ] was wound into a coil and fitted into the sidearm of the reaction system. The vaporization flask was charged with 46.00 g (0.589 mole) of benzene, 77.50 g (0.564 mole) of phosphorus trichloride ($PCl_3$), and a few boiling chips and attached to the quartz tube reactor. The system was flushed with the nitrogen and a trace of aluminum chloride (AlCl₃) sprinkled onto the aluminum wire coil. The sidearm was heated to 99–105° C. and the benzene-PCl₃ mixture heated to reflux to drive the vaporous mixture into the heated sidearm to contact the catalyst contained therein. Droplets of brown-colored oil formed almost immediately on the aluminum wire and flowed down into the vaporization flask and evolution of HCl commenced. At this point the reaction became exothermic and application of heat to the sidearm was discontinued. The temperature in the sidearm maintained itself at 115±5° C. throughout the reaction period. After 7.8 hours, a total of 0.389 mole of HCl had evolved. The reaction mixture in the flask, a dark brown-colored viscous oil, was cooled to ambient temperatures and diluted (incompletely miscible) with 60 ml of benzene. To the benzene-diluted reaction mixture was added 21.6 g (0.245 mole) of p-dioxane (amount calculated from the amount of aluminum wire consumed as determined below) with stirring. A crystalline precipitate formed and the mixture was heated to 70° C., cooled to ambient temperatures, and filtered (under nitrogen) through a Celite filter bed. The filtrate was a clear, red-colored liquid. The precipitate (assumed to be a p-dioxane-AlCl₃ complex) was washed with benzene and the washings added to the filtrate which then separated into two phases. The two phases were separated and analyzed by gas chromatography individually. The upper layer was found to contain 0.027 mole of phenyldichlorophosphine ($C_6H_5PCl_2$), while the lower layer contained 0.077 mole of $C_6H_5PCl_2$. The total isolable yield of $C_6H_5PCl_2$ was 0.104 mole, 26.7% of theory based upon the conversion of PCl₃ as determined by the amount of HCl evolved (0.389 mole). Concentration and vacuum distillation of the phenyldichlorophosphine product mixture may be carried out to yield pure product: $C_6H_5PCl_2$ [bp 140–142° C. (57 mm Hg, 7.60 kPa), Kosolapoff, *Organophosphorus Compounds*, John Wiley & Sons, Inc., New York, 1950, p. 54].

The aluminum wire was removed from the reactor sidearm, cleaned with acetone, and weighed. The weight loss, which corresponds to the amount of aluminum consumed, was 6.58 g (0.244 g-atom). This quantity was used to calculate the amount of p-dioxane required to decompose the aluminum-containing $C_6H_5PCl_2$ complex, assuming a 1/1 mole ratio.

EXAMPLE 2

The reaction system described in Example 1 above was employed. An aluminum wire coil (8.66 g, 0.320 g-atom) was fitted into the sidearm of the system and the vaporization flask was charged with 46.24 g (0.592 mole) of benzene and 78.39 g (0.470 mole) of PCl₃. The system was flushed with nitrogen and a trace of AlCl₃ sprinkled onto the aluminum wire. The sidearm was heated to 134° C. and the benzene-PCl₃ mixture heated to reflux to drive the vaporous mixture into the heated sidearm to contact the catalyst contained therein. The temperature in the sidearm was maintained at 130±5° by applying external heat. After 8.3 hours a total of 0.414 mole of HCl had evolved. The reaction mixture was stripped of unreacted benzene and PCl₃ using water aspirator vacuum. The viscous concentrate was diluted with 30 ml of benzene (immiscible) and 19.27 g (0.219 mole) of p-dioxane added. The crystalline precipitate was filtered off (under nitrogen) through a Celite filter bed and the precipitate washed with benzene, which was added to the filtrate (completely miscible). Gas chromatographic analysis of the filtrate indicated it to contain 0.146 mole of $C_6H_5PCl_2$. The total isolable yield of $C_6H_5PCl_2$ was 0.146 mole, 35.3% of theory based upon the conversion of PCl₃ as determined by the moles of HCl evolved. Separation and purification of the product mixture may be carried out by concentration and vacuum distillation as noted in Example 1 above. The amount of aluminum consumed was 5.88 g (0.218 g-atom).

Thus, it is apparent that there has been provided, in accordance with the present invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the preparation of phenyldichlorophosphine which comprises contacting benzene with phosphorous trichloride in the vapor phase at a temperature from about 100° C. to about 145° C. in the presence of a catalyst consisting essentially of aluminum metal in an amount sufficient to provide from about 0.40 mole to about 0.70 mole per mole of phosphorus trichloride and a catalyst activating amount of aluminum chloride in an amount sufficient to provide from about 0.000010 to about 0.0010 gram per gram of aluminum metal.

2. The process of claim 1 wherein the aluminum metal is a coil of aluminum wire.

3. The process of claim 1 wherein the benzene/phosphorus trichloride mole ratio is from about 1.0 to about 10.0.

4. The process of claim 3 wherein the benzene/phosphorus trichloride mole ratio is from about 3.0 to about 5.0.

5. The process of claim 1 wherein the benzene/phosphorus trichloride reaction is initiated at a temperature of about 100° C.

6. The process of claim 1 wherein the reaction temperature is maintained at about 115±5° C.

7. The process of claim 6 wherein the reaction temperature is maintained by the heat of reaction.

8. The process of claim 1 wherein the reaction temperature is maintained at a temperature in excess of about 120° C. up to about 145° C.

9. The process of claim 8 wherein the reaction temperature is maintained by the addition of heat to the reaction zone.

* * * * *